United States Patent [19]

Pekmez

[11] Patent Number: Plant 7,749

[45] Date of Patent: Dec. 17, 1991

[54] HYBRID TEA ROSE PLANT NAMED PEKCOUJENNY

[76] Inventor: Paul Pekmez, La Petite Pierre, 67290 Wingen-Sur-Moder, France

[21] Appl. No.: 564,418

[22] Filed: Aug. 8, 1990

[51] Int. Cl.[5] ..... A01H 5/00

[52] U.S. Cl. ..... Plt./21

[58] Field of Search ..... Plt. 20, 21, 11, 22, Plt./28, 29

*Primary Examiner*—Howard J. Locker

*Attorney, Agent, or Firm*—Christie, Parker & Hale

[57] ABSTRACT

A new hybrid tea rose with cardinal red flowers.

1 Drawing Sheet

SUMMARY OF THE INVENTION

The present invention relates to a new and distinct variety of rose plant of the hybrid tea rose class which was originated by my crossing as seed parent an unnamed and unpatented seedling of my creation and as pollen parent the variety known as "Korpek". The varietal denomination of this new rose is "Pekcoujenny".

Among the novel characteristics possessed by this new variety which distinguishes it from its parents and all other varieties of which I am aware are its attractive well formed cardinal red flowers borne on a plant particularly suitable for cut flower production. Flowers open well and hold their coloring as blooms age. Asexual reproduction by propagation by budding of the new variety as performed in La Petite Pierre, Wingen-Sur-Moder, France, shows that the foregoing and other distinguishing characteristics come true to form and are established and transmitted through succeeding propagations.

BRIEF DESCRIPTION OF THE ILLUSTRATION

The illustration depicts the true cardinal red flower coloration of the new variety as well as foliage coloration and characteristics, the color depictions of same being as nearly true as is reasonably possible in a color illustration of this character.

DESCRIPTION OF THE NEW VARIETY

Pekcoujenny is an unusually fine hybrid tea rose of cardinal red flower coloration. It is especially well suited for cut flower production under glass and has produced 120 to 140 blooms per square meter of planting per year. Cut flower stems of this variety are 60 to 80 cm in length. The buds are well shaped and of good form and open into exhibition-type blooms. The foliage is dark green, brilliant and dense.

As indicated previously, Pekcoujenny is a very productive cut flower variety for a hybrid tea rose of this coloring. Flower petals assume a velvety dark red appearance and flowers open slowly but retain the attractive dark red coloring upon aging. Plants of the new variety are healthy and robust as well as resistant to common diseases.

The following is a detailed description of my new variety, with color terminology in accordance with The Royal Horticultural Society Colour Chart (R.H.S.C.C.). The terminology used in color description herein refers to plate numbers in the aforementioned color chart.

Parentage: Seedling.

*Seed parent.*—Unnamed seedling.

*Pollen parent.*—"Korpek".

Class: Hybrid tea.

The following information is from observations made of specimens grown outdoors in La Petite Pierre, France.

FLOWER

Blooming habit: Recurrent.

A. Bud:

(1) *Size.*—Medium to large.

(2) *Form.*—Long pointed.

(3) *Color.*—As sepals divide, bud color is near 53A.

(4) *Sepals.*—Longer than bud, single to foliaceous.

(5) *Penduncle.*—Length: Long and in proportion to bloom. Aspect: Straight. Strength: Erect. Color: Near 138B to A.

B. Bloom:

(1) *Size.*—Average size when fully expanded — about 5 to 6 cm.

(2) *Borne.*—Singly, one to a stem, disbudded.

(3) *Form.*—High centered at first, becoming flat. Outer petals roll under.

(4) *Petalage.*—Number of petals under normal conditions — about 40.

(5) *Color.*—After sepals fall and petals unfurl, predominant flower color viewing petal's top surface is cardinal red, near 53A. Color is general and substantially constant.

C. Petals:

(1) *Texture.*—Medium to thick.

(2) *Appearance.*—Inside velvety and outside satiny.

(3) *Form.*—Broad, fan shaped with some indentation or undulation at margin.

(4) *Arrangement.*—Regularly arranged, imbricated.

(5) *Petaloids in center.*—Few.

(6) *Persistence.*—Petals persist and flowers open slowly which is desirable in cut flowers.

(7) *Fragrance.*—Slight.

(8) *Lasting quality.*—Very long lasting on plant and as cut flower.

REPRODUCTION ORGANS

A. Stamens, filaments and anthers:

*Arrangement.*—Regularly arranged around styles.

*Color.*—Orange yellow.

B. Pollen:

*Color.*—Deep yellow.

C. Styles: Medium length.

D. Stigmas:

*Color.*—Orange red.

E. Hips: None observed.

PLANT

A. Form: Well shaped, symmetrical.

B. Growth: Vigorous, Height attained about 60 to 150 cm.

C. Foliage: Compound 3, 5 or 7 leaflets.

(1) *Size.*—Medium to large.

(2) *Quantity.*—Abundant.

(3) *Color.*—New foliage: Upper side — near 139B. Under side — near 139C. Old foliage: Upper side — near 139A. Under side — near 139B.

(4) *Shape.*—Oval, pointed.

(5) *Texture.*—Leathery; upper side is glossy; under side is matte.

(6) *Edge.*—Serrate.

(7) *Serration.*—Ordinary.

(8) *Leaf stem.*—Color — medium green.

(9) *Stipules.*—Medium length, simple.

(10) *Resistance to disease.*—Mildew — Good.

D. Wood (1) *New wood.*—Color — light green. Bark — smooth.

(2) *Old wood.*—Color — medium green. Bark — smooth.

E. Thorns:

*Quantity (main stalk).*—Few.

*On laterals from stalk.*—Few.

*Form.*—Long, thin, straight.

*Length.*—Medium.

*Color.*—Near tan.

*Position.*—Irregular.

*Prickles.*—Few to none present.

F. Winter hardiness: Needs protection in severe climates.

I claim:

1. A new and distinct variety of rose plant of the hybrid tea rose class, substantially as shown and described, suitable for cut flower production and characterized particularly by attractive cardinal red flowers.

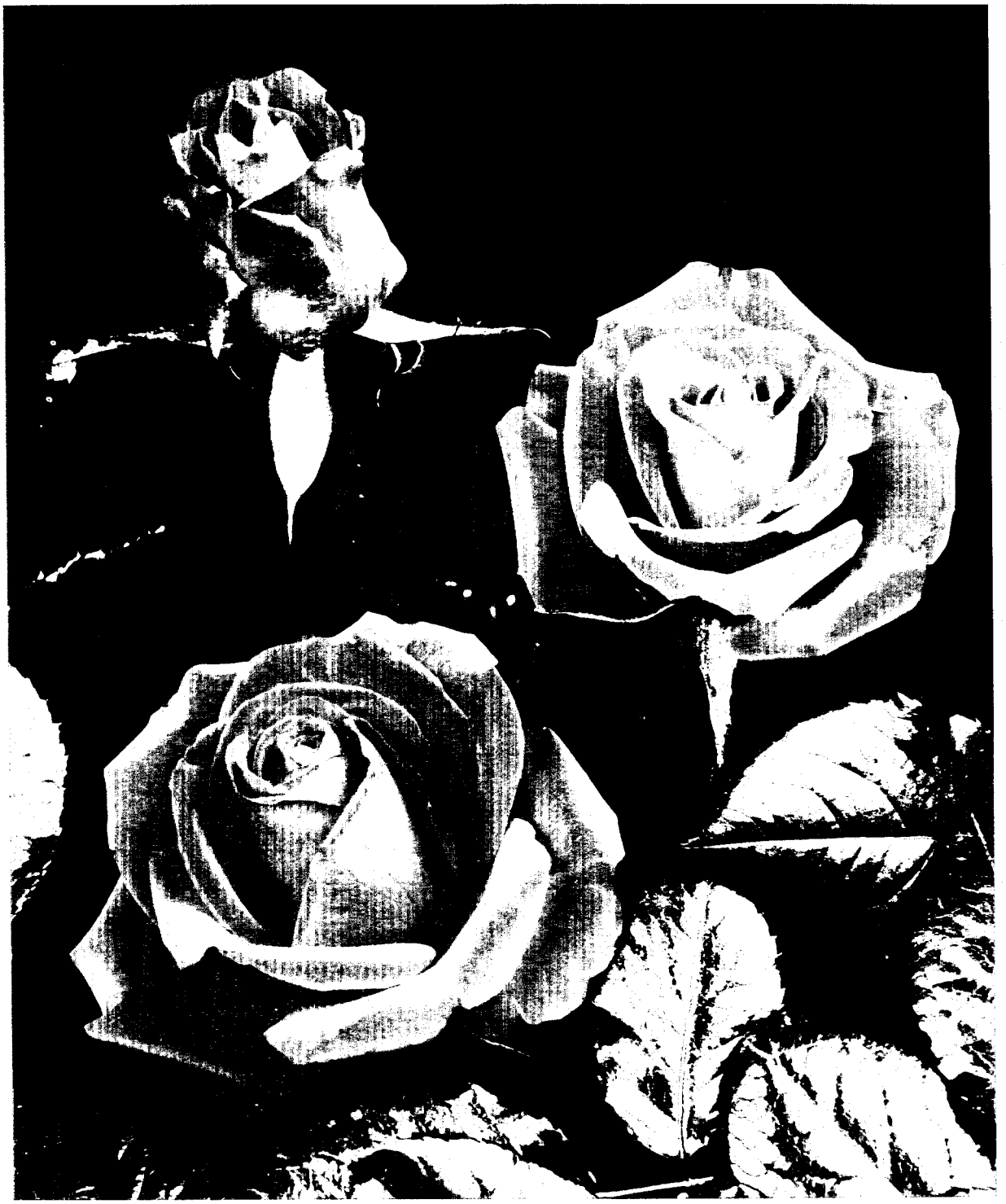

* * * * *